United States Patent [19]

Miescher

[11] Patent Number: 5,049,495

[45] Date of Patent: Sep. 17, 1991

[54] FERMENTATION METHOD FOR PRODUCING POLYETHER ANTIBIOTICS

[75] Inventor: Guido M. Miescher, Terre Haute, Ind.

[73] Assignee: International Minerals & Chemical Corp., Northbrook, Ill.

[21] Appl. No.: 868,016

[22] Filed: May 29, 1986

[51] Int. Cl.$^5$ .............. C12P 17/16; C12P 17/48; C12N 1/38; C07D 407/00

[52] U.S. Cl. .............. 435/118; 435/119; 435/886; 435/244; 549/414

[58] Field of Search .............. 435/118, 253.5, 886, 435/244, 803, 119, 170; 424/123; 549/414

[56] References Cited

U.S. PATENT DOCUMENTS

| | | |
|---|---|---|
| 3,326,775 | 6/1967 | Miescher .............. 195/47 |
| 3,929,575 | 12/1975 | Miescher .............. 195/30 |
| 3,995,027 | 11/1976 | Gale et al. .............. 424/115 |
| 4,009,262 | 2/1977 | Boeck et al. .............. 424/123 |
| 4,033,823 | 7/1977 | Liu et al. .............. 195/80 R |
| 4,033,829 | 7/1977 | Liu et al. .............. 435/118 |
| 4,035,481 | 7/1977 | Berg et al. .............. 424/122 |
| 4,038,384 | 7/1977 | Berg et al. .............. 424/122 |
| 4,085,224 | 4/1978 | Berg et al. .............. 424/283 |
| 4,110,435 | 8/1978 | Nakatsukasa et al. .............. 424/122 |
| 4,110,436 | 8/1978 | Nakatsukasa et al. .............. 424/122 |
| 4,137,241 | 1/1979 | Liu et al. .............. 260/345.7 |
| 4,141,907 | 2/1979 | Nakatsukasa et al. .............. 260/345.7 |
| 4,174,390 | 11/1979 | Hamill et al. .............. 424/117 |
| 4,174,404 | 11/1979 | Nakatsukasa et al. .............. 424/283 |
| 4,204,039 | 5/1980 | Nakatsukasa et al. .............. 435/118 |
| 4,212,942 | 7/1980 | Miyazaki et al. .............. 435/119 |
| 4,214,091 | 7/1980 | Oishi et al. .............. 549/62 |
| 4,221,724 | 9/1980 | Liu et al. .............. 260/345.8 |
| 4,263,427 | 4/1981 | Liu et al. .............. 536/1 |
| 4,266,028 | 5/1981 | Nakamura et al. .............. 435/118 |
| 4,283,493 | 8/1981 | Liu et al. .............. 435/119 |
| 4,294,925 | 10/1981 | Liu et al. .............. 435/84 |
| 4,395,491 | 7/1983 | Hohl et al. .............. 435/262 |
| 4,440,857 | 4/1984 | Seno et al. .............. 435/118 |

FOREIGN PATENT DOCUMENTS 0679087 2/1950 United Kingdom .............. 435/897

OTHER PUBLICATIONS

Stark et al., *Antimicrobial Agents and Chemotherapy*, 1967, pp. 353–358.

Primary Examiner—Douglas W. Robinson
Assistant Examiner—Irene Marx
Attorney, Agent, or Firm—Wendell R. Guffey; Thomas L. Farquer

[57] ABSTRACT

High titers of polyether antibiotics are obtained in a fermentation broth by inoculating a nutrient fermentation broth with a microorganism capable of producing a polyether antibiotic. Growth of the microorganism is established in the broth by incubating the inoculated broth at a physiologically acceptable temperature until pH of the broth begins to rise upon establishment of growth of the microorganism. A free fatty acid then is fed into the broth to achieve and maintain a free fatty acid concentration in the broth of about 0.1% by weight or greater but less than a level at which the free fatty acid is toxic to the microorganism. The free fatty acid is fed into the broth during the remainder of fermentation at about a rate at which the free fatty acid is consumed by the microorganism, to product high titers of the polyether antibiotic.

21 Claims, No Drawings

FERMENTATION METHOD FOR PRODUCING POLYETHER ANTIBIOTICS

BACKGROUND OF THE INVENTION

1. Field of the Invention

The present invention relates to the art of fermenting microorganisms to obtain a desired fermentation product, such as a polyether antibiotic.

2. Description of the Background Art

Fermentation of microorganisms has long been utilized to obtain desired products, making the fermentation art one of the oldest practiced by man.

There are an increasingly large number of products which are obtainable by cultivating naturally occurring or genetically engineered microorganisms such as bacteria. For example, polyether antibiotics are carboxylic acid ionophores which can be produced by culturing Streptomyces type microorganisms. These polyether antibiotics have a basic structure generally consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A generally comprehensive review of this class of antibiotics is set forth in Westley, *Adv. Appl. Microbiology*, 22:177-223 (1977). At least twenty different polyether antibiotics were known at the time the Westley article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyether antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, salinomycin, narasin, lonomycin, X-206, SY-1, noboritomycins A & B, mutalomycin, and alborixin.

Class 1b of the polyether antibiotics are defined by Westley as monovalent monoglycoside polyether antibiotics. These polyether antibiotics, as the class name suggests, include a glycoside type structure, more specifically, a 2,3,6-trideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. Generally, the polyether antibiotics of this class contain about six or seven tetrahydropyran and/or -furan structures. Included within class 1b are the polyether antibiotics septamycin, dianemycin, A-204, lenoremycin, carriomycin and etheromycin.

Class 2a as defined by Westley is directed to divalent polyether antibiotics. These antibiotics have a generally linear configuration, may contain from about two to about three tetrahydropyran and/or -furan structures, up to about three total ring structures and no nitrogen atoms. Included within class 2a are the antibiotics lasalocid and lysocellin.

Westley's class 2b of polyether antibiotics is directed to divalent pyrrole ethers and thus, in contrast to the antibiotics of the other classes, the class 2b antibiotics contain one or more nitrogen atoms. Included within class 2b are the polyether antibiotics X-14547, and A-23187 also known as calcimycin.

Polyether antibiotics have a number of known uses, including treatment of poultry coccidiosis, growth promotion and enhancement of feed efficiency of ruminants, swine and poultry, and control of swine dysentery.

Polyether antibiotics can be obtained by fermenting a nutrient-containing liquid fermentation medium or broth inoculated with a microorganism capable of producing the desired antibiotic. Typical liquid fermentation media are generally aqueous dispersions containing sources of assimilable nitrogen and carbon as is known in the art. The fermentation media can also contain a variety of optional ingredients, if desired, such as for example, pH adjustment agents, buffers, trace minerals, antifoam agents, and the like.

Although it is desirable to produce products such as polyether antibiotics by fermentation of microorganisms, commercial production of fermentation products is not economically advantageous unless the fermentation process is efficient enough to keep the cost of fermentative production below the value of the product produced thereby.

There thus remains a need in the art for increasingly more efficient and cost effective fermentation methods.

SUMMARY OF THE INVENTION

In accordance with the present invention, a method for producing a polyether antibiotic comprises inoculating a nutrient fermentation broth with a microorganism capable of producing a polyether antibiotic during fermentation of the microorganism, the broth having a physiologically acceptable pH and containing sufficient assimilable carbon and other nutrients to establish growth of the microorganism in the broth. Growth of the microorganism is established in the broth by incubating the inoculated broth at a physiologically acceptable temperature until the pH of the broth begins to rise upon establishment of growth of the microorganism in the broth. When the pH of the broth begins to rise upon establishment of growth of the microorganism therein, a free fatty acid is fed into the broth to achieve and maintain a free fatty acid concentration in the broth of about 0.1% by weight or greater but less than a level at which the free fatty acid is toxic to the microorganism. The free fatty acid is fed into the broth during the remainder of the fermentation at about a rate at which the free fatty acid is consumed by the microorganism, to produce the polyether antibiotic.

DETAILED DESCRIPTION OF THE PREFERRED EMBODIMENTS

In order for microorganisms to grow in an aqueous medium, sources of carbon and nitrogen, which are basic biological building blocks, must be available to the microorganism in assimilable form.

When fermenting polyether antibiotic-producing microorganisms to obtain polyether antibiotics, fats and oils are typically utilized as a primary carbon source.

Fats and oils are esters or more specifically triglycerides of fatty acids. However, free fatty acids are generally quite toxic to microorganisms, making them undesirable for use as a primary carbon source in the fermentative production of polyether antibiotics.

Despite the high toxicity of free fatty acids to microorganisms, it has surprisingly been discovered that the growth rate of polyether antibiotic-producing microorganisms can be substantially increased, and higher polyether antibiotic titers in the fermentation broth achieved, when utilizing free fatty acids as a principal carbon source by continuously feeding small amounts of free fatty acids into the fermentation broth during fermentation at about a rate at which the free fatty acids are consumed by the microorganisms.

An assimilable source of nitrogen is also provided in the culture medium. Suitable sources of nitrogen include yeast, yeast-derived products, enzyme-hydrolyzed caseine, peptones, cornmeal, soybean meal, cottonseed meal, amino acids such as glutamic acid, and the like.

Nutrient inorganic salts can also be incorporated in the culture medium such as soluble salts capable of yielding sodium, magnesium, calcium, ammonium, chloride, carbonate, sulfate, nitrate, and like ions. Essential trace elements necessary for the growth and development of the microorganism should also be included in the culture medium. Such trace elements commonly occur as impurities in other constituents of the medium in amounts sufficient to meet the growth requirements of the organism.

Polyether antibiotics are produced by growing the polyether antibiotic-produced microorganism in an aerated, agitated, submerged culture with the pH of the broth adjusted to about neutral, i.e., from about 6.5 to about 7.5. Fermentation can generally be carried out at slightly elevated temperatures, e.g., between about 25° C. and 35° C. Incubation of the broth can be carried out for a period of several days, e.g., from about 4 to 12 days or longer if it is economically advantageous to do so.

It may be necessary to add small amounts (i.e., 0.2 ml/1) of an anti-foam agent such as polypropylene glycol to large-scale fermentation media if foaming becomes a problem. Excessive foaming may occur, for example, when fatty acids are added initially to the fermentation broth as the principal carbon source.

In accordance with one embodiment, a nutrient fermentation broth is inoculated with a microorganism capable of producing a polyether antibiotic, such as a lysocellin-producing strain of *Streptomyces cacaoi* var. *asoensis*. Preserved seed cultures of the production strain (e.g., preserved in glycerol at −80° C.) are advantageously initially developed in a first stage inoculation medium on a small scale. For example, the content of a capsule containing 1 ml of a glycerol seed culture can be added to 80 ml first stage inoculation medium in a 500 ml Erlenmeyer flask, the first stage inoculation medium containing 2% by weight glycerol, 1% by weight bacto peptone, 1% by weight bacto meat extract and balanced tap water. The flask is incubated on a rotary action (approximately 350 rpm) shaker at about 28°-38° C. for about 48 hours (until satisfactory growth is established).

At this point, the seed culture can be used immediately to inoculate a second stage inoculum, or it can be stored at 1°-4° C. up to 3 days for later use.

For cultivation of a second stage inoculum, 2.5% of the first stage inoculum is added to 100 ml second stage inoculum medium in a 500 ml Erlenmeyer flask, the second stage inoculum medium containing 2.5% by weight soybean oil, 2.5% by weight soybean flour, 0.15% by weight $KH_2PO_4$, 0.15% by weight $K_2HPO_4$, and trace element sources $FeSO_4 \cdot 7H_2O$ (5 ppm), $MnSO_4 \cdot H_2O$ (1.5 ppm), $CoCl_2 \cdot 6H_2O$ (0.5 ppm), and distilled water (if tap water is used, only 0.5 ppm $CoCl_2$ is added as trace element source). The flask is incubated on a rotary action shaker (approximately 350 rpm) at 28°-30° C. for about 24 hours. Advantageously, the second stage inoculum is transferred immediately from the shaker to a primary fermentation medium in a main fermenter.

The primary fermentation medium or broth has a physiologically acceptable pH (e.g., about neutral pH) and contains sufficient assimilable carbon and other nutrients to establish growth of the microorganism in the primary broth.

The primary fermentation broth typically contains a triglyceride oil as an initial assimilable carbon source for establishing growth of the microorganism in the broth. Triglycerides which are suitable for use according to the present invention as initial carbon sources include soybean oil, safflower oil, cottonseed oil, sesame oil, olive oil, rape oil, peanut oil, corn oil, sunflower oil, and like vegetable oils, cod oil and like fish oils, and lard and like animal-fat-and-oils. Vegetable oils are a preferred carbon source, with soybean oil being particularly preferred.

Other known carbon sources, including free fatty acids, can be utilized as a initial principal carbon source for establishment of growth of the microorganism in the primary fermentation broth, but free fatty acids are not a preferred initial carbon source since their use may result in excessive foaming of the fermentation broth.

In accordance with one embodiment, a primary fermentation broth having a 10-12-liter volume which is suitable for inoculation by 200 milliliters of the second stage inoculum described above from two second stage inoculum flasks, includes 4.5% by weight soybean flour, 3% by weight soybean oil, 0.05% by weight $KH_2PO_4$, 0.15% by weight $K_2HPO_4$, 1 ppm $CoCl_2 \cdot 6H_2O$, up to about 0.1% by weight Hodag antifoam K-67 and tap water to a 10-12 liter volume.

The inoculated primary medium is incubated at a physiologically acceptable temperature (e.g., 28°-30° C.) under suitable conditions of aeration and agitation to establish growth of the microorganism in the broth. A rise in pH is a suitable "marker" which can be utilized to pinpoint the development stage of the fermentation, i.e., establishment of growth of the microorganism in the broth. This typically takes place about 15-20 hours after inoculation, and marks the point at which continuous feeding of free fatty acid into the broth is begun.

After establishment of growth of the microorganism in the primary fermentation broth is indicated by a rise in pH, free fatty acids are fed into the primary broth to maintain a free fatty acid concentration in the broth of about 0.1% by weight or more but less than a level at which the free fatty acid is toxic to the microorganism. The free fatty acid is fed into the broth during the remainder of the fermentation at about a rate at which the free fatty acid is consumed by the microorganism.

Free fatty acids which are suitable for use according to the present invention include saturated fatty acids such as lauric acid, myristic acid, palmitic acid, stearic acid, arachidic acid, lignoceric acid and the like, and unsaturated fatty acids such as palmitoleic acid, oleic acid, linoleic acid, linolenic acid, arachidonic acid and the like.

According to one embodiment, unsaturated fatty acids are continuously fed into the fermentation broth as a principal carbon source during fermentation after establishment of growth of the microorganism in the broth.

In a particularly preferred embodiment, oleic acid is fed at a rate of about 0.5% by weight per day into the fermentation broth after pH of the fermentation begins to rise upon establishment of growth of the microorganism in the broth, to achieve and maintain an oleic acid concentration in the broth of from about 0.1% to about 0.4% by weight during the fermentation. During fermentation, oleic acid concentration in the broth is monitored to maintain the concentration within the desired range. Oleic acid concentration can be monitored, for example, utilizing a high performance liquid chromotography assay for oleic acid.

In other embodiments, a triglyceride oil such as soybean oil is fed into the broth during fermentation along with a free fatty acid such as oleic acid in a respective ratio by weight of oleic acid to soybean oil of from about 4:1 to about 3:2. For example, suitable ratios by weight of oleic acid to soybean oil for feeding to a fermentation broth as principal carbon sources are respectively 80:20, 70:30, 60:40, 40:60 and the like.

According to one embodiment, free fatty acid feeding into the broth is terminated near the end of fermentation (or after a predetermined antibiotic titer has been achieved), and the broth is harvested upon substantial depletion of remaining carbon source in the broth. This allows spray- or drum-drying of the whole fermentation broth to produce an economical biomass product containing polyether antibiotic.

The present invention substantially increases polyether antibiotic titers in fermentation broths during cultivation of polyether antibiotic-producing microorganisms, as compared to utilization of triglycerides alone as a principal carbon source. For example, a lysocellin fermentation containing 10% soybean oil in the medium yielded 15 grams per liter lysocellin, with approximately 3% of the soybean oil not being utilized. The same medium containing 3% soybean oil in the medium and having 7% of oleic acid continuously fed during the fermentation yielded 20 grams per liter lysocellin. The same medium containing 3% soybean oil in the medium and having 7% of methyl oleate continuously fed during the fermentation yielded only 5 grams per liter lysocellin, with most of the methyl oleate not being utilized.

The exact reasons why continuous feeding of free fatty acids produce substantially higher polyether antibiotic titers than use of triglycerides as a primary carbon source are not known. Without being bound to any particular theory, it is believed that microorganisms must first hydrolyze triglycerides utilizing a lipase enzyme, and that this hydrolysis step during metabolism of triglycerides may be a growth rate-limiting step.

The invention is further illustrated by the following examples which are not intended to be limiting.

EXAMPLE I

Seed Development

Capsules of seed culture of a lysocellin-producing strain of S. cacaoi var. asoensis containing 1 ml of culture in glycerol were stored at −80° C. The content of one capsule was added to 80 ml first stage inoculum medium in a 500 ml Erlenmeyer flask. The medium contained (in wt. %) glycerol (2%), Bacto Peptone (1%), Bacto Meat Extract (1%), and tap water to volume. The flask was incubated on a rotary action shaker (~350 rpm) at 28°–30° C. for 48 hours (until satisfactory growth was established), and this seed was used immediately to inoculate the second stage inoculum as follows.

2.5 Percent of the first stage inoculum was added to 100 ml second stage inoculum medium in each of several 500 ml Erlenmeyer flasks. The medium contained (by wt. %) soybean oil (2.5%), soybean flour (2.5%), $KH_2PO_4$ (0.15%), $K_2HPO_4$ (0.15%), and the trace elements $FeSO_4 \cdot 7H_2O$ (5 ppm), $MnSO_4 \cdot H_2O$ (1.5 ppm), $CoCl_2 \cdot 6H_2O$ (0.5 ppm), and distilled water. The flasks were incubated on rotary action shakers (~350 rpm) at 28°–30° C. for about 24 hours. The second stage inoculum was transferred immediately from shaker to fermenter.

EXAMPLE II

Main Fermentation

In separate fermentations, 200 milliliters from 2 flasks of the second stage inoculum were used (~2% wt.) to inoculate a 20-liter sterilized fermenter containing (by wt. %) as "standard" principal medium soybean flour (4.5%), soybean oil (3%), $KH_2PO_4$ (0.05%), $K_2HPO_4$ (0.15%), and $CoCl_2 \cdot 6H_2O$ (1 ppm). Hodag K-67 antifoam (about 0.1%) and tap water to about a 10 liter volume. The pH of the inoculated medium was about neutral and did not require any further pH adjustment.

The physical parameters for fermentations using a New Brunswick fermenter were as follows:

| | |
|---|---|
| Medium, volume | 10,000 ml |
| Air | 10 l/min (5 l/min during first 16 hr) |
| PSI g | 4 |
| Agitation | 2 impellors, 10.8 cm diam. |
| RPM | 650 |
| Temperature | 29-30° C. |

Oleic acid alone, mixtures of oleic acid and soybean oil or soybean oil alone was fed into the various fermentation broths when the pH of the fermentations began to rise, indicating the development stage of the fermentation (about 15–20 h after inoculation). The feed rate was about 0.5% (wt.) per day to maintain an oleic carbon source concentration in the medium in the range between 0.1 and 0.4%.

The fermentation results are shown in Table 1 below, which indicates the feed mixture used and final lysocellin titers.

TABLE 1

Final Lysocellin Titers in Fermentation Using Various Feeding Combinations of Oleic Acid and Soy Oil

| Batch No. | Variation Medium | Final Lysocellin Titer g/l | Initial Soy Oil in Medium % | Feed Mixture Soy Oil % | Feed Mixture Oleic Acid % |
|---|---|---|---|---|---|
| *100% Oleic Acid Fed* | | | | | |
| 1 | a | 35 | 3 | 0 | 100 |
| 2 | b | 29 | 3 | 0 | 100 |
| *20% Soybean Oil/80% Oleic Acid Fed* | | | | | |
| 3 | none | 29 | 3 | 20 | 80 |
| 4 | none | 26 | 3 | 20 | 80 |
| 5 | c | 36 | 3 | 20 | 80 |
| *30% Soybean Oil/70% Oleic Acid Fed* | | | | | |
| 6 | c | 29 | 3 | 30 | 70 |
| *40% Soybean Oil/60% Oleic Acid Fed* | | | | | |
| 7 | none | 32 | 3 | 40 | 60 |
| 8 | none | 36 | 3 | 40 | 60 |
| *60% Soybean Oil/40% Oleic Acid Fed* | | | | | |
| 9 | none | 19 | 3 | 60 | 40 |
| *100% Soybean Oil Used* | | | | | |
| 10 | a | 19 | 7.5 | (no feed) | |
| 11 | a | 19 | 7.5 | (no feed) | | a Medium contains soy flour (4.5%), soy oil (according to table), $KH_2PO_4$ (.1%), $K_2HPO_4$ (.2%), $CaCO_3$ (.4%), $FeSO_4 \cdot 7H_2O$ (50 ppm), and $CoCl_2 \cdot 6H_2O$ (2 ppm), with tap water.
b Medium contains soy flour (4.5%), soy oil (according to table), $KH_2PO_4$ (.05%), $K_2HPO_4$ (.15%), $CoCl_2 \cdot 6H_2O$ (1 ppm), with tap water.
c Only variation from "standard" medium described above is 0.4% soy flour.

The above table demonstrates the substantial higher lysocellin titers obtainable by continuously feeding oleic acid to the fermentation as a principal carbon source.

What is claimed is:

1. A method for producing the polyether antibiotic lysocellin comprising:
   (a) inoculating a nutrient fermentation broth with a Streptomyces microorganism capable of producing the polyether antibiotic lysocellin during fermentation of said microorganism, the broth having a physiologically acceptable pH and containing sufficient assimilable carbon and other nutrients to establish growth of the microorganism in the broth;
   (b) establishing growth of the microorganism in the broth by incubating the inoculated broth at a physiologically acceptable temperature until the pH of the broth begins to rise upon establishment of growth of the microorganism in the broth;
   (c) feeding a free fatty acid into the broth when the pH of the broth begins to rise upon establishment of growth of the microorganism, to achieve and maintain a free fatty acid concentration in said broth of about 0.1% by weight or greater but less than a level at which said free fatty acid is toxic to said microorganism, wherein said free fatty acid is fed into said broth during the remainder of fermentation at about a rate at which said free fatty acid is consumed by said microorganism, to produce said polyether antibiotic.

2. The method of claim 1 wherein said assimilable carbon is present in a triglyceride oil.

3. The method of claim 2 wherein said free fatty acid is an unsaturated free fatty acid.

4. The method of claim 3 wherein said triglyceride oil is soybean oil and said free fatty acid is oleic acid.

5. The method of claim 1 wherein said physiologically acceptable pH is about neutral.

6. The method of claim 1 wherein prior to the inoculating step, the fermentation broth contains about 3% by weight soybean oil as a source of said assimilable carbon.

7. The method of claim 1 wherein the feeding step is begun about 15-20 hours after the inoculating step.

8. The method of claim 4 wherein during the feeding step, the concentration of oleic acid in the broth is maintained at about 0.1-0.4% by weight.

9. The method of claim 4 wherein the fermentation is complete within about two weeks.

10. The method of claim 4 wherein during the feeding step, soybean oil is fed into the broth with said oleic acid in a ratio by weight of oleic acid to soybean oil respectively of from about 4:1 to about 3:2.

11. The method of claim 10 wherein during the feeding step oleic acid and soybean oil are fed into the broth in a respective ratio by weight of about 60:40.

12. The method of claim 10 wherein during the feeding step oleic acid and soybean oil are fed into the broth in a respective ratio by weight of about 70:30.

13. The method of claim 10 wherein during the feeding step oleic acid and soybean oil are fed into the broth in a respective ratio by weight of about 80:20.

14. The method of claim 1 further including the steps of terminating feeding of free fatty acid into the broth near the end of fermentation and harvesting the broth after substantial depletion of the carbon source in the broth.

15. The method of claim 1 wherein said Streptomyces microorganism is a lysocellin producing strain of *Streptomyces cacaoi* var. asonensis.

16. A method for producing the polyether antibiotic lysocellin comprising:
   (a) inoculating a nutrient fermentation broth with a microorganism from the strain *Streptomyces cacaoi* var. asonensis, said microorganism being capable of producing the polyether antibiotic lysocellin during fermentation of said microorganism, the broth having a physiologically acceptable pH and containing sufficient assimilable carbon and other nutrients to establish growth of the microorganism in the broth;
   (b) establishing growth of the microorganism in the broth by incubating the inoculated broth at a physiologically acceptable temperature until the pH of the broth begins to rise upon establishment of growth of the microorganism in the broth;
   (c) feeding a free fatty acid into the broth when the pH of the broth begins to rise upon establishment of growth of the microorganism, to achieve and maintain a free fatty acid concentration in said broth of about 0.1% by weight or greater but less than a level at which said free fatty acid is toxic to said microorganism, wherein said free fatty acid is fed into said broth during the remainder of fermentation at about a rate at which said free fatty acid is consumed by said microorganism, to produce said polyether antibiotic.

17. The method of claim 16 wherein said assimilable carbon is present in a triglyceride oil.

18. The method of claim 17 wherein said free fatty acid is an unsaturated free fatty acid.

19. The method of claim 18 wherein said triglyceride oil is soybean oil and said free fatty acid is oleic acid.

20. The method of claim 16 wherein said physiologically acceptable pH is about neutral.

21. The method of claim 16 wherein during the feeding step, the concentration of oleic acid in the broth is maintained at about 0.1-0.4% by weight.

* * * * *